United States Patent
Hsu et al.

(10) Patent No.: US 11,610,312 B2
(45) Date of Patent: Mar. 21, 2023

(54) IMAGE PROCESSING APPARATUS FOR EVALUATING CARDIAC IMAGES AND VENTRICULAR STATUS IDENTIFICATION METHOD

(71) Applicant: Acer Incorporated, New Taipei (TW)

(72) Inventors: Hung-Sheng Hsu, New Taipei (TW); Chien-Hung Li, New Taipei (TW); Yi-Jin Huang, New Taipei (TW)

(73) Assignee: Acer Incorporated, New Taipei (TW)

( * ) Notice: Subject to any disclaimer, the term of this patent is extended or adjusted under 35 U.S.C. 154(b) by 73 days.

(21) Appl. No.: 17/233,558

(22) Filed: Apr. 19, 2021

(65) Prior Publication Data

US 2022/0292680 A1 Sep. 15, 2022

(30) Foreign Application Priority Data

Mar. 10, 2021 (TW) .................... 110108496

(51) Int. Cl.
*G06T 7/00* (2017.01)
*G06T 7/20* (2017.01)
(Continued)

(52) U.S. Cl.
CPC .......... *G06T 7/0014* (2013.01); *A61B 8/5223* (2013.01); *G06T 7/20* (2013.01);
(Continued)

(58) Field of Classification Search
USPC ................................ 382/128, 131
See application file for complete search history.

(56) References Cited

U.S. PATENT DOCUMENTS

| 8,150,513 B2 * | 4/2012 | Chinchoy ............ A61N 1/3627 607/9 |
| 9,033,887 B2 * | 5/2015 | Lonasec ................. A61B 8/488 600/441 |

(Continued)

FOREIGN PATENT DOCUMENTS

| CN | 110664435 | 1/2020 |
| TW | 202022713 | 6/2020 |

OTHER PUBLICATIONS

Petrank et., Using Anatomical Marker for Left Ventricular Segmentation of Long Axis Ultrasound Images, arXiv:1510.03250v1 [cs.CV] http://doi.org/10.48550/arXiv.1510.03250, pp. 1-11. (Year: 2015).*

*Primary Examiner* — Ishrat I Sherali
(74) *Attorney, Agent, or Firm* — JCIPRNET (57) ABSTRACT

An image processing apparatus for evaluating cardiac images and a ventricular status identification method are provided. In the method, a region of interest (ROI) is determined from multiple target images, a variation in grayscale values of multiple pixels in the ROIs of each target image is determined, and one or more representative images are obtained according to the variation in the grayscale values. The target image is related to the pixels within an endocardial contour of a left ventricle. A boundary of the ROI is approximately located at two sides of a bottom of the endocardial contour. The ROI corresponds to a mitral valve. The variation in the grayscale values is related to a motion of the mitral valve. The representative image is for evaluating a status of the left ventricle.

8 Claims, 5 Drawing Sheets

(51) Int. Cl.
*A61B 8/08* (2006.01)
*G06V 10/25* (2022.01)
(52) U.S. Cl.
CPC ............ *G06V 10/25* (2022.01); *A61B 8/0883* (2013.01); *G06T 2207/30048* (2013.01); *G06V 2201/031* (2022.01)

(56) References Cited

U.S. PATENT DOCUMENTS

2007/0014452 A1 1/2007 Suresh et al.
2008/0085043 A1* 4/2008 Watanabe ............... G06T 7/149
382/131

* cited by examiner

IMAGE PROCESSING APPARATUS FOR EVALUATING CARDIAC IMAGES AND VENTRICULAR STATUS IDENTIFICATION METHOD

CROSS-REFERENCE TO RELATED APPLICATION

This application claims the priority benefit of Taiwan application serial no. 110108496, filed on Mar. 10, 2021. The entirety of the above-mentioned patent application is hereby incorporated by reference herein and made a part of this specification.

BACKGROUND

Technical Field

This disclosure relates to an image identification technology, and in particular to an image processing apparatus for evaluating cardiac images and a ventricular status identification method.

Description of Related Art

In clinical practice, there are many ways to assess a status of a heart currently. One of them is to measure a left ventricular ejection fraction (LVEF), that is, to measure how much blood is ejected from the left ventricle in every heartbeat. It should be noted that the measurement of the left ventricular ejection fraction requires reference to an end-systolic volume (ESV) and an end-diastolic volume (EDV). Therefore, it is necessary to identify end-systole (ES) and end-diastole (ED) in a heart rate cycle before the Simpson formula can be applied to calculate the EDV and the ESV. The conventional technology can identify the ED based on an R wave in an electrocardiogram (ECG), which is when volume of the left ventricle is at its largest. In addition, ES can be recognized at the end of a T wave of the ECG; which is when the volume of the left ventricle is at its smallest. However, it is not easy to identify the ES in the ECG

SUMMARY

In view of this, the embodiments of the disclosure provide an image processing apparatus for evaluating cardiac images and a ventricular status identification method, which can quickly and accurately identify the end-systole (ES) and the end-diastole (ED).

The ventricular status identification method according to the embodiment of the disclosure includes (but is not limited to) the following steps. A region of interest is determined from multiple target images. The target images target pixels within an endocardial contour of the left ventricle, a boundary of the region of interest is approximately located on two sides of a bottom of the endocardial contour, and the region of interest corresponds to a mitral valve. A variation in grayscale values of the multiple pixels in the region of interest in the target images is determined. The variation in the grayscale values is related to a motion of the mitral valve. One or more representative images are obtained according to the variation in the grayscale values. The representative images are for assessing a status of a left ventricle.

The image processing apparatus used for evaluating cardiac images according to the embodiment of the disclosure includes (but is not limited to) a storage device and a processor. The storage device stores program codes. The processor is coupled to the storage device, and is configured to load and execute the program codes to determine an region of interest from multiple target images, determine a variation in grayscale values of multiple pixels in the region of interest in the target images, and obtain one or more representative images according to the variation in the grayscale values. The target images target pixels within an endocardial contour of a left ventricle, a boundary of the region of interest is approximately located on both sides of a bottom of the endocardial contour, and the region of interest corresponds to a mitral valve. The variation in the grayscale values is related to a motion of the mitral valve. The representative images are for assessing a status of the left ventricle.

Based on the above, in the image processing apparatus for evaluating the cardiac images and the ventricular status identification method according to the embodiments of the disclosure, the motion of the mitral valve in the region of interest is analyzed according to the variation in the grayscale values, and the representative images are determined accordingly. The representative images may be further used for assessing the status of the left ventricle. The opening and the closing of the mitral valve are related to the end-systole and the end-diastole. In this way, the different statuses of the ventricle can be identified quickly and accurately.

To make the aforementioned more comprehensible, several embodiments accompanied with drawings are described in detail as follows.

DESCRIPTION OF THE EMBODIMENTS

Figure 1:
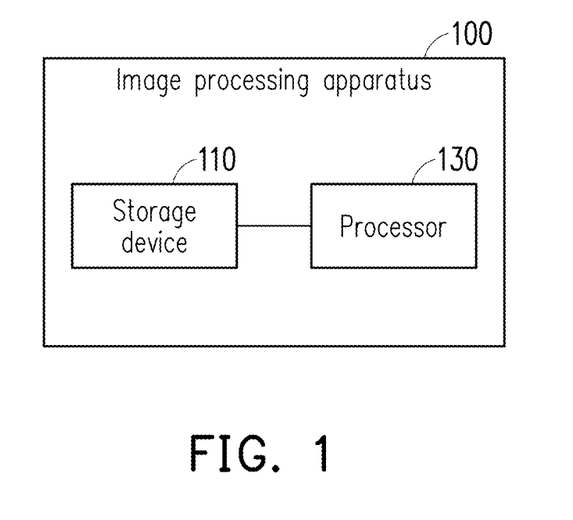
FIG. 1 is a block diagram of components of an image processing apparatus according to an embodiment of the disclosure.

FIG. 1 is a block diagram of components of an image processing apparatus 100 according to an embodiment of the disclosure. With reference to FIG. 1, the image processing apparatus 100 includes (but is not limited to) a storage device 110 and a processor 130. The image processing apparatus 100 may be a desktop computer, a notebook computer, a smart phone, a tablet computer, a server, a medical testing instrument, or other computing apparatuses.

The storage device 110 may be any type of fixed or removable random access memory (RAM), a read-only memory (ROM), a flash memory, a hard disk drive (HDD), a solid-state drive (SSD), or similar components. In an embodiment, the storage device 110 is configured to record a program code, a software module, a configuration, data (such as an image, a grayscale value, a statistical value, a status, or a volume, etc.), or files, and will be described in detail later.

The processor 130 is coupled to the storage device 110, and the processor 130 may be a central processing unit (CPU), a graphics processing unit (GPU), or other programmable general-purpose or special-purpose microprocessors, a digital signal processor (DSP), a programmable controller, a field-programmable gate array (FPGA), an application-specific integrated circuit (ASIC), a neural network accelerator, or other similar components, or a combination of the above components. In an embodiment, the processor 130 is configured to execute all or some of operations of the image processing apparatus 100, and may load and execute various program codes, software modules, files, and data recorded by the storage device 110.

Hereinafter, a method according to the embodiment of the disclosure is described in conjunction with various apparatuses, components, and modules in the image processing apparatus 100. Each process in the method can be adjusted according to an implementation situation, and is not limited thereto.

Figure 2:
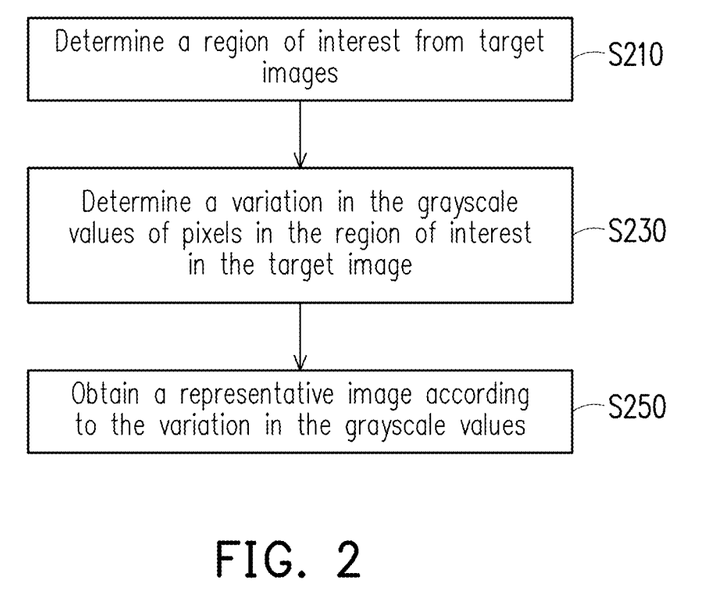
FIG. 2 is a flowchart of a ventricular status identification method according to an embodiment of the disclosure.

FIG. 2 is a flowchart of a ventricular status identification method according to an embodiment of the disclosure. With reference to FIG. 2, the processor 130 may determine a region of interest (ROI) from multiple target images (Step S210). Specifically, the target images target pixels within an endocardial contour of a left ventricle. In an embodiment, the processor 130 may obtain A4C (apical four chamber view) or A2C (apical two chamber view) cardiac ultrasound images (or known as echocardiography) of one or several heart rhythm cycles in continuous frames. A source of the cardiac ultrasound images in the continuous frames may be a video taken targeting the heart that is segmented into continuous frames of cardiac images, or multiple frames of cardiac images detected by an ultrasound probe and transmitted through wireless or wired transmission. In addition, continuous images refer to the multiple cardiac images captured by the ultrasound probe at a specific frame rate and sorted by time.

In an embodiment, the processor 130 may input the A4C or A2C cardiac ultrasound images to a machine learning model (such as a multilayer perceptron (MLP) or a support vector machine (SVM) based on deep learning) to segment an image within the endocardial contour of the left ventricle and output it to serve as an endocardial image of the left ventricle. In other embodiments, the processor 130 may identify the endocardial contour based on Scale-invariant feature transform (SIFT), Haar feature, AdaBoost, or other identification technology, and segment to obtain the target image accordingly.

Figure 3:
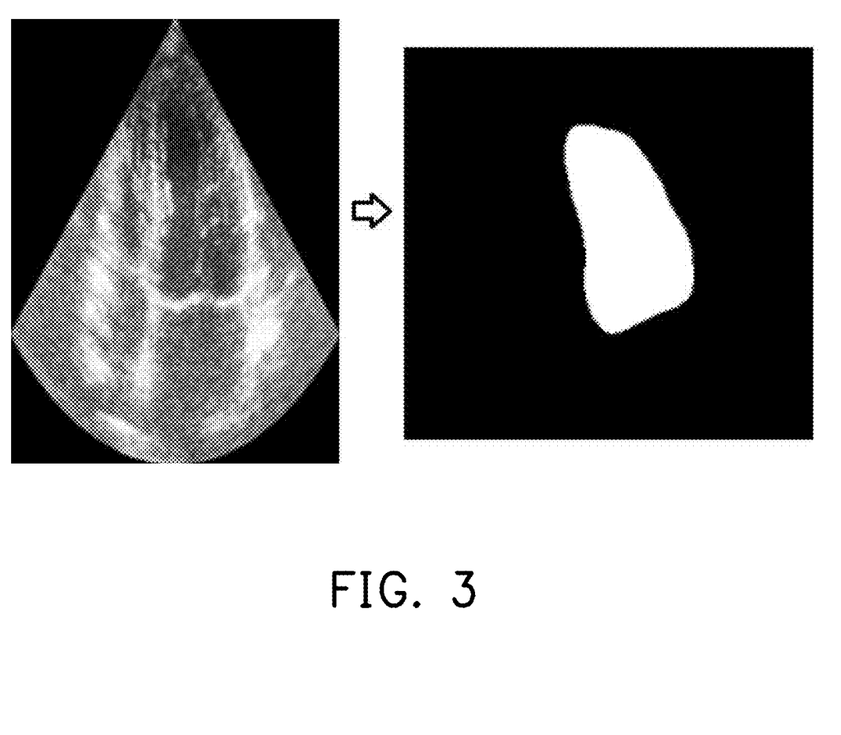
FIG. 3 is a schematic diagram of the segmented left ventricle according to an embodiment of the disclosure.

FIG. 3 is a schematic diagram of the segmented left ventricle according to an embodiment of the disclosure. With reference to FIG. 3, the left image shows an A2C cardiac ultrasound image, which may be identified to obtain the endocardial contour of the left ventricle as shown in the right image. The processor 130 may segment the target image from the cardiac ultrasound image based on the endocardial contour. It should be noted that FIG. 3 shows the image segmentation of a single frame, and the same or similar means may also be used for segmentation of other frames.

In some embodiments, the processor 130 may also directly obtain the target image that has been segmented from the cardiac image. That is, other devices or medical instruments have segmented to obtain the target image first.

In an embodiment, a boundary of the region of interest is approximately located on two sides of a bottom of the endocardial contour, and the region of interest corresponds to a mitral valve. The bottom refers to a lower half of an endocardium, or other proportions, or ranges.

In an embodiment, the processor 130 may determine the region of interest on a binary image of the endocardial contour. There are only two grayscale values in the binary image (such as grayscale values of all black and all white). Therefore, the processor 130 may respectively start calculating coordinates position (that is, corresponding to two sides of the bottom) of a first left pixel and a first right pixel from the bottom of the left ventricle endocardium. The positions of the two pixels are left and right boundaries of the region of interest. The boundaries on the two sides are approximately located on a leftmost side of the anterior leaflet and a rightmost side of the posterior leaflet of the mitral valve in the A4C or A2C view.

In an embodiment, a thickness of the region of interest (that is, a width in a vertical direction in the A4C or A2C view, or top and bottom boundaries) may be a thickness of the anterior leaflet or the posterior leaflet of the mitral valve. It should be noted that different people may have different thickness due to factors such as age and gender. For example, the thickness of the anterior leaflet of a person younger than 20 years old is 1.3 millimeter (mm), the thickness of the anterior leaflet of a person between 20 and 56 years old is 1.6 mm, and the thickness of the anterior leaflet of a person older than 60 years is 3.2 mm.

Figure 4A:
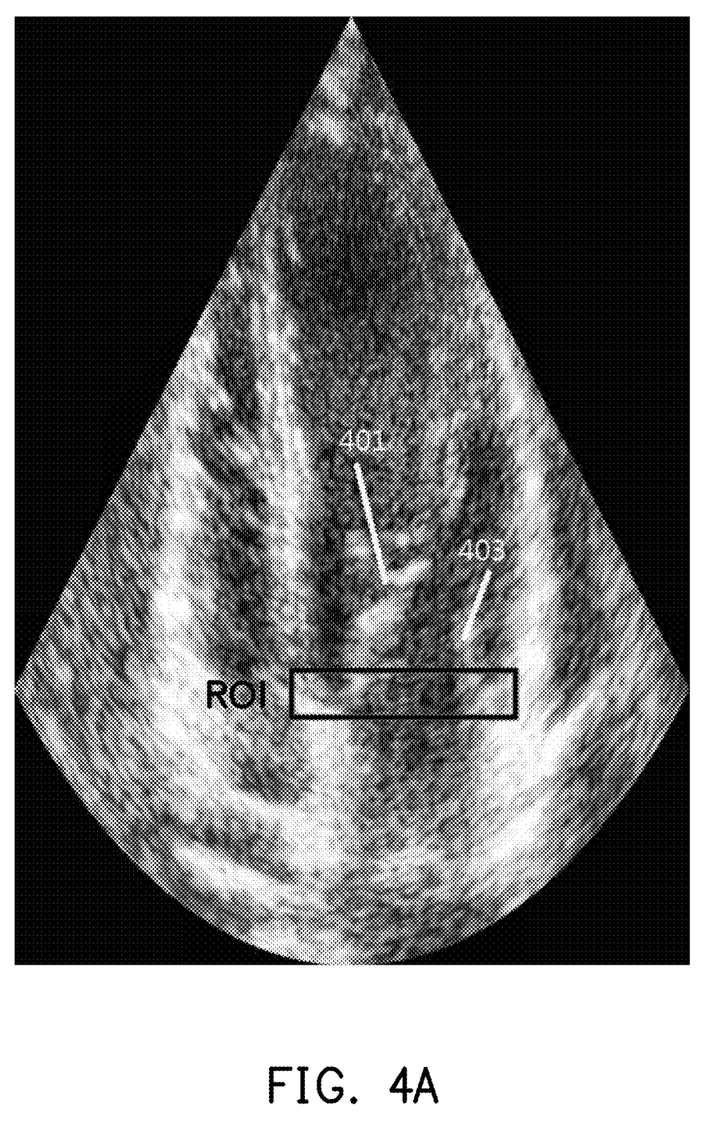
FIG. 4A is a schematic diagram of an end-diastole (ED) of the left ventricle according to an embodiment of the disclosure.

FIG. 4A is a schematic diagram of an end-diastole (ED) of the left ventricle according to an embodiment of the disclosure. With reference to FIG. 4A, a region of interest ROI shown in the figure approximately corresponds to an anterior leaflet 401 and a posterior leaflet 403. A left boundary of the region of interest ROI corresponds to a leftmost side of the anterior leaflet 401, and a left boundary of the region of interest ROI corresponds to a rightmost side of the posterior leaflet 403. A thickness of the region of interest ROI is slightly greater than or approximately equal to thicknesses of the anterior leaflet 401 and the posterior leaflet 403.

It should be noted that a shape of the region of interest ROI is not limited to the rectangle shown in FIG. 4A. In other embodiments, the region of interest may be a geometric shape such as an ellipse or a rhombus, or an irregular shape corresponding to a contour of the mitral valve.

In another embodiment, the processor 130 may determine the boundary of the region of interest based on an image identification technology (such as a neural network or a feature comparison). For example, the processor 130 determines the region of interest based on a classifier derived from training samples that have marked a position of the mitral valve or based on image features of the mitral valve. The region of interest approximately corresponds to the contour of the mitral valve when it is fully opened.

The processor 130 may determine a variation in the grayscale values of multiple pixels in the region of interest in the target image (Step S230). Specifically, the variation in the grayscale values is related to a motion of the mitral valve. The mitral valve of the heart opens and closes with contraction and relaxation of the heart. The cardiac images in the continuous frames show a process of the mitral valve from fully opened to fully closed (or from fully closed to fully opened). It should be noted that the A4C or A2C cardiac ultrasound images usually adopt B-mode. Therefore, when the ultrasonic probe emits a sound wave, an intensity of an echo reflected back may be represented by a brightness of a point. An image composed of the points (serving as pixels) is a grayscale image. In the grayscale image, the intensity (that is, the grayscale value) of each of the pixels is a value from 0 to 255, where the value of 0 represents a blackest point and the value of 255 represents a whitest point. As shown in FIG. 4A, the mitral valve (composed of the anterior leaflet 401 and the posterior leaflet 403) is approximately white.

Focusing on the region of interest (that is, only analyzing or viewing images in the region of interest), the motion of the mitral valve enables different surface areas of the mitral valve of in the image to appear in the region of interest. For example, a portion of the anterior leaflet or a portion of the posterior leaflet gradually moves away from the region of interest in the process of the mitral valve changing from fully opened to fully closed.

In an embodiment, the processor 130 may determine a sum of the grayscale values of the pixels in the region of interest in each of the target images. It should be noted that the surface area of the mitral valve included in the region of interest in the different target images may be different. The mitral valve in the grayscale image is approximately white (that is, the grayscale value is high), and its surroundings are approximately black (that is, the grayscale value is low). The sum of the gray scale values may reflect the surface area of the mitral valve included in the region of interest. The processor 130 may determine a difference in the sums among the target images (that is, a variation in the surface areas of the mitral valve included in the region of interest), and this difference corresponds to the variation in the grayscale values. That is, the difference in the sums of the grayscale values is in response to the motion of the mitral valve.

Figure 4B:
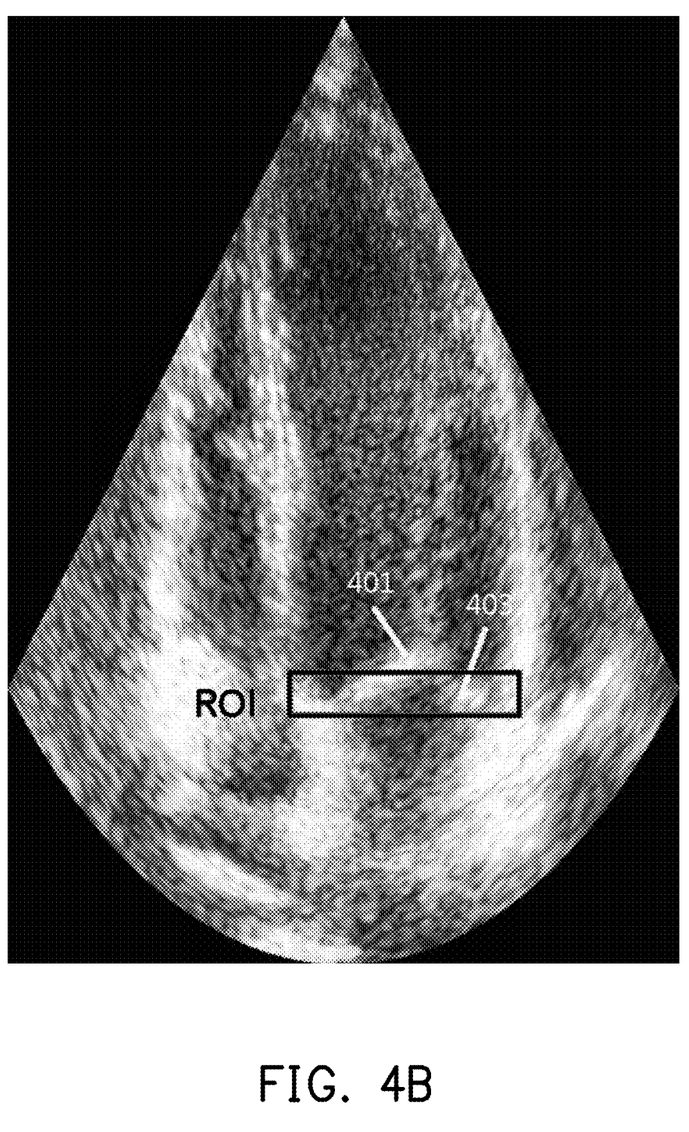
FIG. 4B is a schematic diagram of the left ventricle from the end-diastole to the end-systole (ES) according to an embodiment of the disclosure.
Figure 4C:
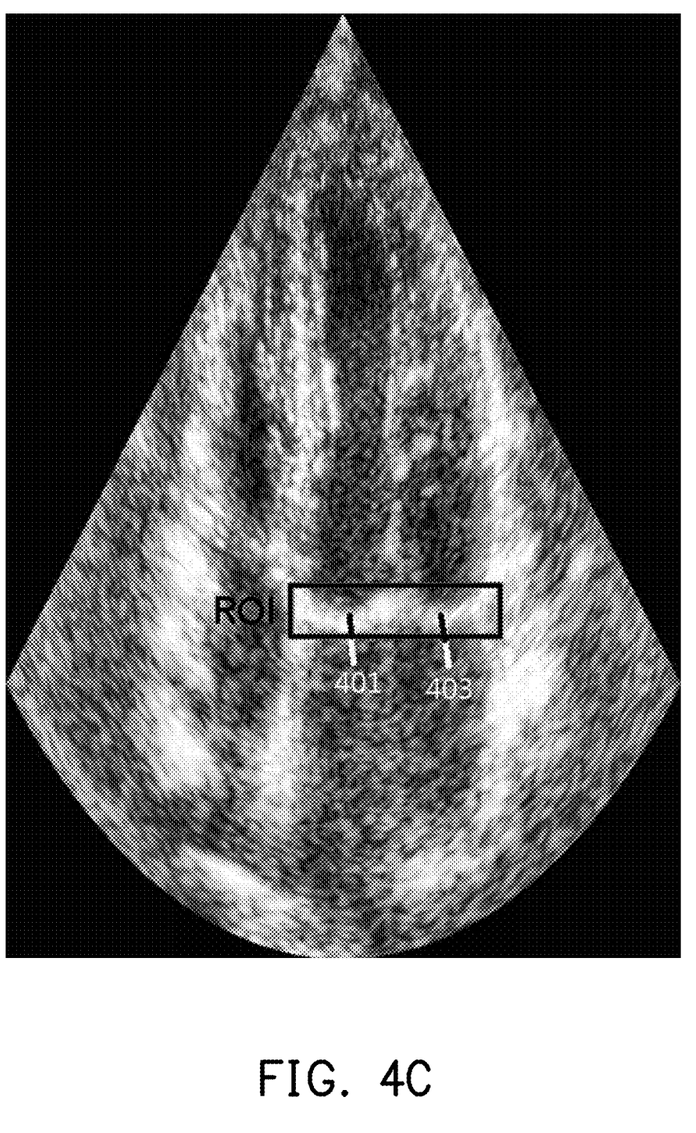
FIG. 4C is a schematic diagram of the end-systole of the left ventricle according to an embodiment of the disclosure.

For example, FIG. 4B is a schematic diagram of the left ventricle from the end-diastole and an end-systole according to an embodiment of the disclosure, and FIG. 4C is a schematic diagram of the end-systole of the left ventricle according to an embodiment of the disclosure. With reference to FIGS. 4A to 4C, surface areas of the anterior leaflet 401 and the posterior leaflet 403 included in the region of interest ROI may be different during the contraction and relaxation of the heart.

In some embodiments, the processor 130 may increase contrast of the target image through histogram equalization or other image processing, and then determine the sum of the grayscale values of the pixels.

In an embodiment, the processor 130 may determine a largest and a smallest in the sums among the target images. The difference in the foregoing sums is related to the largest sum and the smallest sum. It should be noted that in clinical practice, when the mitral valve is fully closed, it is the end-diastole (ED) of the heart, and when the mitral valve is fully opened, it is the end-systole (ES) of the heart. The smallest sum of the grayscale values in the region of interest corresponds to a status where the mitral valve is completely closed, that is, corresponds to the end-diastole of the left ventricle. The largest sum corresponds to a status where the mitral valve is fully opened, that is, corresponds to the end-systole of the left ventricle. The processor 130 may use the largest sum and the smallest sum of the grayscale values to serve as representations of the variation in the grayscale values. That is, the processor 130 uses the end-diastole and the end-systole to serve as representations.

In some embodiments, the processor 130 may calculate an average value of the sums of the grayscale values or a number of the largest grayscale values, and determine a largest and a smallest among the target images accordingly. For example, the average value of the sums corresponding to the end-diastole is the smallest, and the average value of the sums corresponding to the end-systole is the largest. Or, the number of the largest grayscale values corresponding to the end-diastole is the least, and the number corresponding to the end-systole is the most.

The processor 130 may obtain one or more representative images according to the variation in the grayscale values (Step S250). Specifically, the representative images may be for assessing a status of the left ventricle. In the clinical practice, a volume of the left ventricle in an end-diastole status is the largest (as shown in FIG. 4A), and the volume of the left ventricle in the end-systole status is the smallest (as shown in FIG. 4C). In an embodiment, the processor 130 may obtain the target image with the largest sum of the grayscale values and the target image with the smallest sum of the grayscale values, so as to serve as the representative images. That is, the two representative images respectively correspond to the end-systole status and the end-diastole status.

It can be seen from this that the embodiment of the disclosure may determine whether the target image is an end-systole image or an end-diastole image of the heart according to a variation in the motion of the mitral valve in the region of interest. Compared with analyzing a septal annulus, the embodiments of the disclosure can quickly identify the end-systole or the end-diastole. For example, in a heart rate cycle, the disclosure can recognize the end-systole status or the end-diastole status.

In an embodiment, the processor 130 may respectively calculate the volume of the left ventricle in the representative image, and determine a variation in the volume of the left ventricle between the foregoing largest and smallest (that is, a difference in the volume between the largest and the smallest). For example, the processor 130 may calculate a surface area occupied by the pixels within the endocardial contour representing the left ventricle in the image. In addition, the variation in the volume is for evaluating an amount of blood ejected. For example, the processor 130 may determine a left ventricular ejection fraction (LVEF) according to an end-systolic volume (ESV) and an end-diastolic volume (EDV).

In other embodiments, according to different requirements, the processor 130 may also obtain the target image of the ventricle in other statuses according to the different sums of the grayscale values, so as to serve as the representative image.

It should be noted that the embodiments of the disclosure may identify the end-systole or the end-diastole of the heart from the cardiac images in real time or non-real time. In an embodiment, in real time, the ultrasound probe transmits several frames of heart images. Therefore, the processor 130 may accumulate a number of the frames of several heart rate cycles before it is able to identify the end-systole or end-diastole. In another embodiment, the processor 130 may segment the A4C or A2C cardiac ultrasound video into several cardiac images, extract the cardiac images of the frames of several heartbeat cycles, and then further identify the end-systole or end-diastole.

In summary, in the image processing apparatus for evaluating the cardiac images and the ventricular status identification method according to the embodiments of the disclosure, the variation in the grayscale values of the pixels in the region of interest in the image are analyzed so as to obtain the motion of the mitral valve in the region of interest. In addition, the embodiment of the disclosure may identify the status of the heart in the end-systole or the end-diastole based on the sum of the grayscale values of the pixels, and evaluates the amount of the blood ejected accordingly. In this way, the different statuses of the heart in the process of contraction and relaxation can be quickly and accurately identified.

Although the disclosure has been described with reference to the above-mentioned embodiments, it is not intended to be exhaustive or to limit the disclosure to the precise form or to exemplary embodiments disclosed. It is apparent to one of ordinary skill in the art that modifications to the described embodiments may be made without departing from the spirit and the scope of the disclosure. Accordingly, the scope of the disclosure is defined by the claims appended hereto and their equivalents in which all terms are meant in their broadest reasonable sense unless otherwise indicated.

What is claimed is:

1. A ventricular status identification method, comprising:
   determining a region of interest from a plurality of target images, wherein the target images target pixels within an endocardial contour of a left ventricle, a boundary of the region of interest is approximately located on two sides of a bottom of the endocardial contour, and the region of interest corresponds to a mitral valve;
   determining a variation in grayscale values of a plurality of pixels in the region of interest in the target images, wherein the variation in the grayscale values is related to a motion of the mitral valve; and
   selecting a first target image having the largest statistical value and a second target image has the smallest statistical value from the plurality of target images as representative images according to the variation in the grayscale values, wherein the variation between the first target image and the second target image is a difference between the largest statistical value and the smallest statistical value in the grayscale values of the region of interest among the plurality of target image, the largest statistical value represents a largest area of the mitral valve included in the region of interest, the smallest statistical value represents a smallest area of the mitral valve included in the region of interest, and the at least one representative images are used for evaluating a status of the left ventricle.

2. The ventricular status identification method according to claim 1, wherein determination of the variation in the grayscale values of the pixels in the region of interest in the target images comprises:
   determining a sum of the grayscale values of the pixels in the region of interest; and
   determining a difference in the sums among the target images, wherein the difference corresponds to the variation in the grayscale values.

3. The ventricular status identification method according to claim 2, wherein determination of the difference in the sums among the target images comprises:
   determining a largest in the sums among the target images as the largest statistical value and a smallest in the sums among the target images as the smallest statistical value, wherein the difference is related to the largest and the smallest in the sums, the smallest statistical value corresponds to an end-diastole (ED) of the left ventricle, and the largest statistical value corresponds to an end-systole (ES) of the left ventricle; and
   using the largest and the smallest in the sums to serve as representations of the variation in the grayscale values.

4. The ventricular status identification method according to claim 1, further comprising:
   determining a variation in a volume of the left ventricle between the largest and the smallest, wherein the variation in the volume is for evaluating an amount of blood ejected.

5. An image processing apparatus for evaluating cardiac images, comprising:
   a storage device, storing a plurality of program codes; and
   a processor, coupled to the storage device, and configured to load and execute the program codes, so as to:
     determine a region of interest from a plurality of target images, wherein the target images target pixels within an endocardial contour of a left ventricle, a boundary of the region of interest is approximately located on two sides of a bottom of the endocardial contour, and the region of interest corresponds to a mitral valve;
     determine a variation in grayscale values of a plurality of pixels in the region of interest in the target images, wherein the variation in the grayscale values is related to a motion of the mitral valve; and
     select a first target image having a largest statistical value and a second target image having a smallest statistical value from the plurality of target images as representative images according to the variation in the grayscale values, wherein the variation between the first target image and the second target image is a difference between the largest statistical value and the smallest statistical value in the grayscale values of the region of interest among the plurality of target image, the largest statistical value represents a largest area of the mitral valve included in the region of interest, the smallest statistical value represents a smallest area of the mitral valve included in the region of interest, and the at least one representative images are used for evaluating a status of the left ventricle.

6. The image processing apparatus for evaluating cardiac images according to claim 5, wherein the processor is further configured to:
   determine a sum of the grayscale values of the pixels in the region of interest; and
   determine a difference in the sums among the target images, wherein the difference corresponds to the variation in the grayscale values.

7. The image processing apparatus for evaluating cardiac images according to claim 6, wherein the processor is further configured to:
   determine a largest in the sums among the target images as the largest statistical value and a smallest in the sums among the target images as the smallest statistical value, wherein the difference is related to the largest and the smallest in the sums, the smallest statistical value corresponds to an end-diastole of the left ventricle, and the largest statistical value corresponds to an end-systole of the left ventricle; and
   use the largest and the smallest in the sums to serve as representations of the variation in the grayscale values.

8. The image processing apparatus for evaluating cardiac images according to claim 6, wherein the processor is further configured to: determine a variation in a volume of the left ventricle between the largest and the smallest, wherein the variation in the volume is for evaluating an amount of blood ejected.

* * * * *